(12) United States Patent
Elmaleh et al.

(10) Patent No.: US 11,679,243 B2
(45) Date of Patent: Jun. 20, 2023

(54) NON-DIGESTIBLE, CONTROLLED RELEASE SYSTEM FOR SOLUBLE DRUG DELIVERY

(71) Applicants: David R. Elmaleh, Newton, MA (US); Doron Weinfeld, Tel-Aviv (IL)

(72) Inventors: David R. Elmaleh, Newton, MA (US); Doron Weinfeld, Tel-Aviv (IL)

( * ) Notice: Subject to any disclaimer, the term of this patent is extended or adjusted under 35 U.S.C. 154(b) by 244 days.

(21) Appl. No.: 16/870,691

(22) Filed: May 8, 2020

(65) Prior Publication Data

US 2020/0353233 A1 Nov. 12, 2020

Related U.S. Application Data

(60) Provisional application No. 62/844,897, filed on May 8, 2019.

(51) Int. Cl.
*A61M 31/00* (2006.01)

(52) U.S. Cl.
CPC ................ *A61M 31/002* (2013.01)

(58) Field of Classification Search
CPC ............. A61M 31/002; A61M 2210/1042
See application file for complete search history.

(56) References Cited

U.S. PATENT DOCUMENTS

2007/0202151 A1* 8/2007 Lee .............. A61M 31/002
424/426

* cited by examiner

*Primary Examiner* — Bradley J Osinski
(74) *Attorney, Agent, or Firm* — Pearl Cohen Zedek Latzer Baratz LLP (57) ABSTRACT

A single or multi layered device (hereinafter alternately referred to as a "capsule") of non-digestible material encapsulating an ingestible drug solution capable of slow solution release of stable solubilized drugs in water, saline, a buffer or lipophilic acceptable carriers. Methods for preparing the same and for safe, nearly constant dispensing of drugs following capsule swallowing. A safe, controlled flow release mechanism for the capsule's drug to the gastric system is disclosed.

8 Claims, 10 Drawing Sheets

NON-DIGESTIBLE, CONTROLLED RELEASE SYSTEM FOR SOLUBLE DRUG DELIVERY

CROSS-REFERENCE TO RELATED APPLICATIONS

This application claims the benefit of U.S. Provisional Patent Application No. 62/844,897, filed May 8, 2019, which is hereby incorporated by reference in its entirety.

BACKGROUND OF THE INVENTION

Trillions of worldwide drug and supplement pills, capsules, caplets, pastilles, etc., are used daily to treat maladies, prevent diseases (such as heart attack and stroke), as well as, for example, to control excessive metabolic production of cholesterol, glucose, or steroids, control or balance symptoms like pain, body temperature, and neurodegeneration effects, or provide over the counter vitamins, anti-aging substances, and additive supplements.

However, drug use is often associated with side effects. The unwanted effects of pill use include toxic and other side effects resulting from their acute or chronic use depending on the drug target and its treatment.

The chronic—and, many times, excessive—use of daily, repeated doses may be dictated by the pharmacokinetics of a given drug. Doses are scheduled as required to maintain blood plasma levels, tissue targeting, biochemical pathway effects, enzymatic function, or other physiological effects for treatment, while causing some negative effects to the untargeted surroundings. Repeated dosing is often required. Toxicity and other side effects many times desensitize or overwhelm the required effects and have to be discontinued. In other cases, the drug dose is required a drug to be reduced or increased to achieve efficacy. These changes in drug dosing are not side effect free or overall efficacy free.

Drug selectivity and specificity is almost never perfect and causes side effects and toxicity. Therefore, methods for slow or controlled release of drugs, such as degradable and biodegradable polymers, were developed and commercialized as new drug formulations. Other new nanotechnologies and slow release drug delivery systems were and are being developed and commercialized. In many instances, these recent developments claim higher efficiency and lower frequency of dosing. However, these solutions are imperfect and have, associated with the technology, issues with polymer size, complexity of implementation, low effectiveness, kidney and other toxicities, and cost burdens.

The present invention is directed to methods and apparatus to allow the oral and enteric delivery of drugs, which may be soluble in water, saline, buffer, or an acceptable lipophilic carrier. Said invention is directed towards simple to use methods that do not require patient training.

SUMMARY OF THE INVENTION

In the preferred embodiment, the invention comprises a liquid in plastic capsule, swallowing of which is done as required by any other capsule or pill known to the art. In another embodiment, the capsule is filled with pressurized liquid followed by pressurized air or other compatible gas to allow full capsule liquid emptying.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION OF THE INVENTION

In the following description, various aspects of the present invention may be described. For purposes of explanation, specific configurations and details are set forth in order to provide a thorough understanding of the present invention. However, it may also be apparent to one skilled in the art that the present invention may be practiced without the specific details presented herein. Furthermore, well known features may be omitted or simplified in order not to obscure the present invention.

In one embodiment, the device comprises a mechanical delivery system. Said mechanical delivery system comprises at least one bio-compatible, elastic, plastic tube filled with a drug or drugs, with or without pharmaceutically acceptable excipients, and has a fill side and a release side. When filled, the plastic capsule is shaped so as to allow for swallowing by a patient.

In another embodiment, the device comprises a mechanical delivery system. Said mechanical delivery system comprises at least two bio-compatible, elastic, plastic tubes with different elastic flexibilities. One of the tubes is an inner tube filled with a drug, with or without pharmaceutically acceptable excipients, that has a fill side and a release side. The inner tube will contain the drug, and may contain water, saline, a buffer, and/or other pharmaceutically acceptable excipients. The inner tube is filled under pressurized conditions (liquid and/or air). The other tube is an outer tube that comprises at least one layer of much less flexible material that keeps the capsule shape and size constant.

In some embodiments, the capsule tubing may have one or two nozzles for fill and release. The nozzles may be located in the front or back of the elastic tube for fill and/or release of the drug solution. In another embodiment, the nozzles are flush with the capsule ends or extended of the capsule front and back. In another embodiment, the nozzle fill and release tubes are protected from potential irritation of the user's capsule path tissues.

In some embodiments, the front and back openings will be closed after filling and have a mechanism that allows start of drug release pre- or post-swallowing. The filling and emptying system may be a metallic or a non-metallic, non-flexible release tubing with micro opening diameters.

In some embodiments, the micro fill diameter is larger to allow for fast filling. In some embodiments, filling includes air pressurizing. Filling could be with two different functions and fits of tubing. The fill side should include a one way valve. After the completion of filling with the liquid, and optional gas (preferably an inert gas like nitrogen) the fill nozzle is blocked. In some embodiments, the release nozzle side is metallic or non-metallic non-flexible tubing extension (proffered all one plastic mold) with a diameter that allows slow release for 24 to 48 hours while in the gastric system.

In some embodiments, the filled capsule will be for oral delivery.

In preferred embodiments, delivery of the drug from the non-digestible capsule is complete when the pressure inside the capsule is substantially the same as the pressure in the surrounding gastrointestinal environment. In a preferred embodiment the introduction of air or other compatible gas pressure into to the filled capsule allows full capsule emptying. After delivery of the drug is complete, the non-indigestible capsule will exit the patient's body as part of the patient's feces.

In certain embodiments, the capsule skeleton is comprised of an inert biocompatible and stable FDA approved elastomers such as Polydimethylsiloxane (PDMS/dimethicone/E900) in various elasticity molds.

In certain embodiments, the capsule comprises a one way filling valve, sealed by a closure device (rigid ring), made of any FDA approved metals, plastics, glass, ceramics, etc. A release nozzle is preferably made of FDA approved plastic (size accuracy to the microns).

Figure 1:
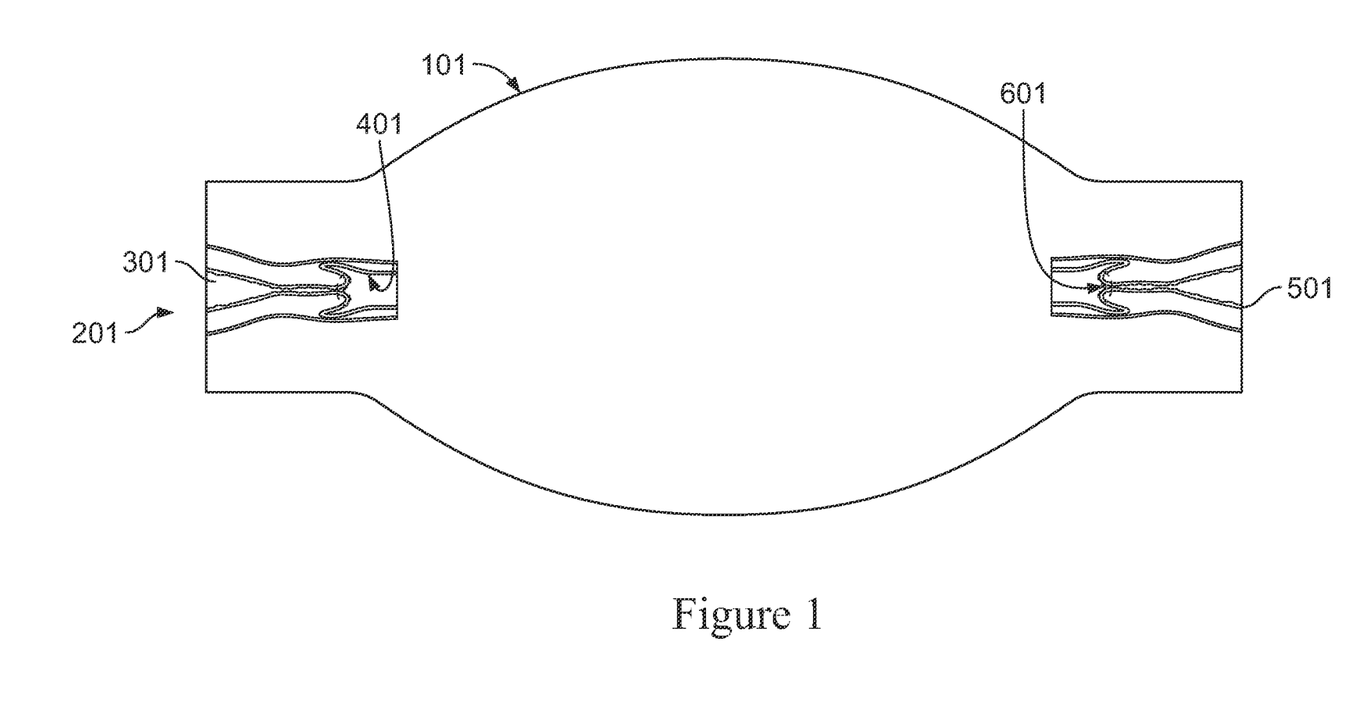
FIG. 1 shows a non-limiting exemplary architecture of a single layered capsule in accordance with some embodiments of the invention.
Figure 2:
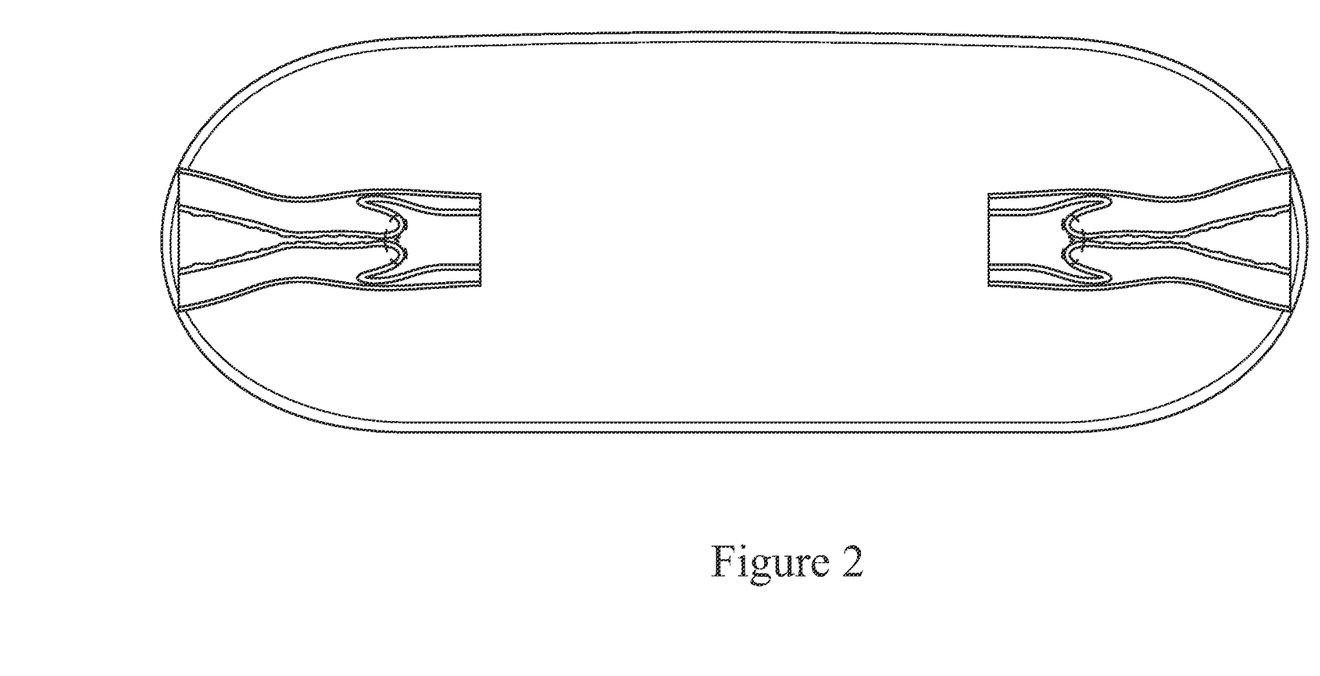
FIG. 2 shows a non-limiting exemplary architecture of a multilayer tubing capsule for oral soluble drug delivery in accordance with some embodiments of the invention.

FIGS. 1 and 2 are systems with filling nozzle and the delivery nozzle serve both function for filling and delivery.

FIG. 1 shows a non-limiting exemplary architecture of a single layered capsule in accordance with some embodiments of the invention. A tube (101—semi flexible FDA biocompatible elastomer, e.g., Polydimethylsiloxane (PDMS/dimethicone/E900), holds the drug or drug solution and becomes shaped like a pill by the process of being filled. The moderate flexibility of the tube post fill provides the pressure for release of the drug. Tube 101 has a filling nozzle (201)–a rigid head as part of the inner tubing that contains a micro tube extension (301) for filling the tube (101) via pressurizing by an outside injector (401)+gas pressure following fill. The outside injector unit is may be controlled manually or may automatically deliver the drug or drug solution into a nozzle unit that fits the micro tube extension (301). The rigid head (201) could be flushed with the pill end or extended of the pill end but protects the tissues in its path from irritation or potential injury. The controlled injector filling unit (401).

After the introduction of the drug or drug solution to the tube (101), a sealing mechanism is used—for example, gluing an easy cover release, pinching or flattening, or having a one way filling path of the micro tube unit (301)). The shape of solution delivery nozzle (501) could be similar to the filling nozzle (201). However, in certain embodiments, the micro-tube delivery may be much narrower, depending on the release flow required to empty the unit in the required time, which may be 24 or 48 hours. The solution delivery nozzle (501) may be sealed while the capsule filling is done. The micro seal may be, for example, a screw that the fits the section (601) or a pull mechanism that allows seal removal before oral administration.

Administration of the drug is activated by opening the delivery mechanism seal and swallowing the capsule, as done with any oral pill.

FIG. 2 shows a non-limiting exemplary architecture of a multilayer tubing capsule for oral soluble drug delivery in accordance with some embodiments of the invention. In certain embodiments, the capsule may have an inner tube (100—flexible FDA biocompatible elastomer, i.e., Polydimethylsiloxane (PDMS/dimethicone/E900), and an outer tube (200), which may be less flexible, tubing shaped similarly to a pill or capsule post filling. Said tube is needed to pressurize the inner tube for release of the solubilized drug. The capsule may have a filling nozzle (300)–a rigid head, part of the inner tubing, that contains a micro tube extension (400) for filling the inner tube (100) via pressurizing by outside injector (500). The outside injector unit may be controlled manually or may automatically deliver the drug solution into the nozzle unit that fits the micro tube extension (400). The rigid tube (200) could be flush with the pill end or extended of the pill end, but protects the tissues in its path from irritation or potential injury. The capsule also has a controlled injector filling unit (500).

After the inner tube (200) is filled, a sealing mechanism is used—for example, gluing a cover, pinching, flatting, or having a one way filling path of the micro tube unit (300)), the micro tube extension (400)). The shape of solution delivery nozzle (600) may be similar to the filling nozzle (300). However, the delivery micro-tube may be much narrower. The degree of narrowing depends on the rate of flow required to empty the unit in the required time, which may be between 24 and 48 hours. The delivery nozzle (600) may be sealed while the capsule filling is done. The micro seal may be, for example, a screw in the fit section (700) or a pull mechanism to allow seal removal before oral administration.

Administration of the drug is activated by opening the delivery mechanism (700) seal and swallowing the capsule, as done with any oral pill.

Figure 3:
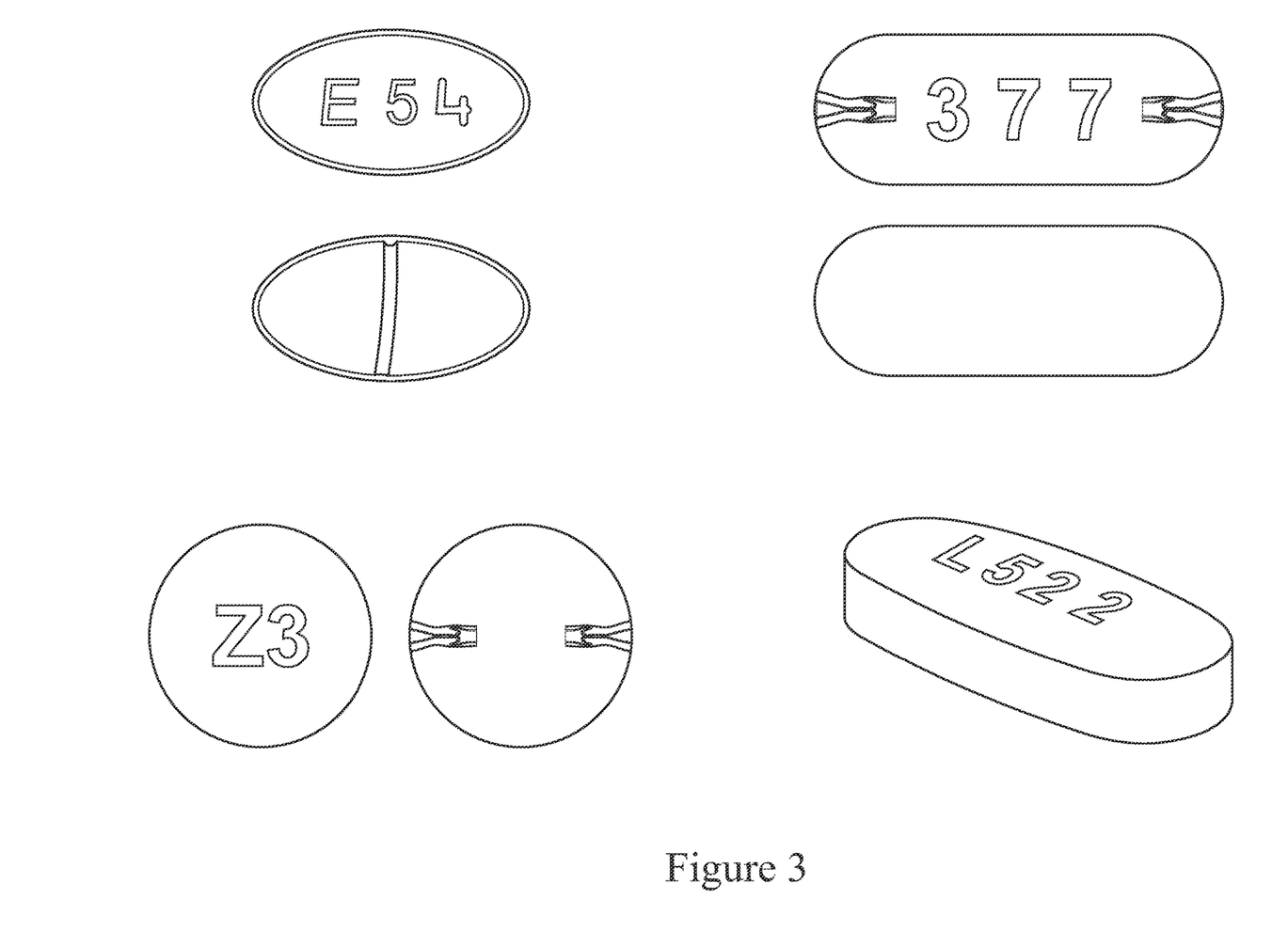
FIG. 3 shows non-limiting exemplary pill shapes in accordance with some embodiments of the invention.

FIG. 3 shows a non-limiting exemplary architecture of a one sided fill/release single or multilayer tubing of a capsule pill for oral soluble drug delivery. Capsules can have various pill shapes following solution filling.

Figure 4:
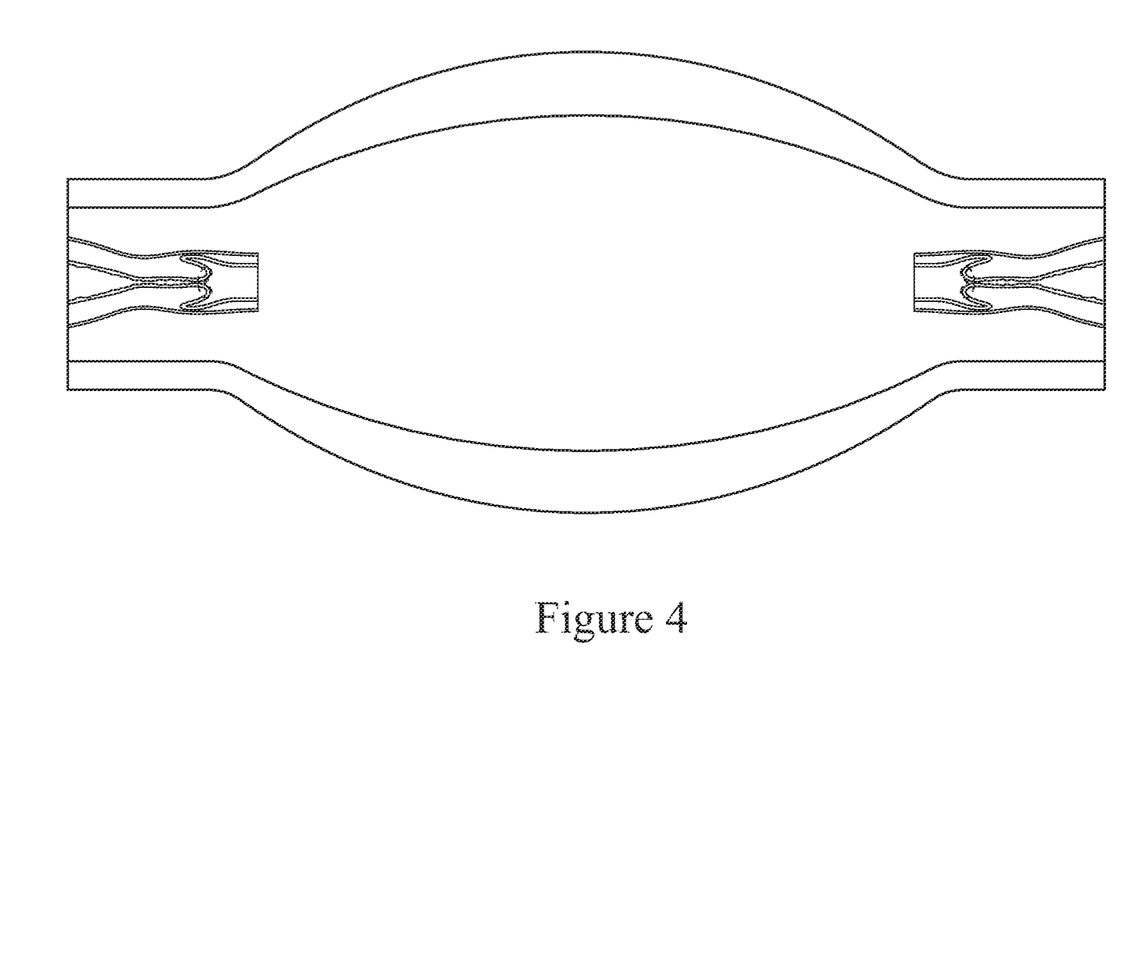
FIG. 4 shows a non-limiting exemplary architecture of a double layered capsule in accordance with some embodiments of the invention.

FIG. 4 shows a non-limiting exemplary architecture of the inner tube of FIG. 1 or the tube of FIG. 2 already first filled with the drug, with or without pharmaceutically acceptable excipients, in a powder or concentrated form. Sterile saline or water are injected to the tubes prior to the device being swallowed. This allows the use of drugs that are unstable, decompose, oxidize or become toxic in an aqueous environment.

In certain embodiments, this invention is a multipurpose carrier and delivery device for many water soluble drugs that can be orally administered. Other structurally modified capsules inert to lipophilic drugs, or drugs requiring lipid formulation, could have similar designs.

Any encapsulated device contemplated by this invention initiates its slow release of solution by an exclusively physical mechanism. The device's ability to release its contents is activated when a simple seal is removed from the device.

Swallowing of the device initiates its constant solution release in the gastric system. The movement of the capsule via the gastric system and the dose amount released in any particular part of the gastric system is not affected by the surrounding physical or chemical properties, such as, taste, pH, osmotic pressure, and reduce the potential toxic side effects from a large bolus dose release of currently available formulations. The inert capsule protects the patient from a rapid, massive dose of the drug or drugs contained therein. In certain embodiments, the rate at which the contents of the device are released may be constant and is determined by the rate of flow from the capsule. Said rate is a direct function of the diameter of the release tube, the pressure of the drug load in the capsule, and the elasticity of the capsule material.

While an ordinary pill releases its active formulated drug dose as a bolus in the gastric system, depending on capsule or tablet design, the uptake efficiency via the gastric wall may decrease due to the exposure time to the gastric wall. The slow release and movement of the described device allows for a long interaction of a solubilized drug that may increase its efficiency.

The inert capsule solution carrier is independent of pH, enzymes, osmotic pressure, diffusion, membranes, hydrogels and electric energy.

The in vivo drug pharmacokinetics should show a constant or close to constant plasma concentration for the majority of time that the capsule is in the gastric system. The drug release may be designed to allow accurate pharmacokinetic performance of a desired drug.

EXAMPLES

Example 1

Flor Rate Analysis Report

A test was run to determine the best suitable tube size (Orifice size) in order to deliver 5 ml of therapy/water in 24 hours to 48 hours. The equipment and materials used include a Pressure Test Unit (Regulated Pressure Test chamber) and different sized orifice including PEEKsil Orange—A 6 in. long tube with 0.001" orifice; EFD p/n 7018395, tube with 0.008" orifice; EFD p.n; 5130-B, tube with 0.006" orifice; and a custom tube: a 0.003" orifice tube.

Four different orifice size tubes (0.001", 0.006" & 0.008" & 0.003") were tested at different pressure settings to determine the flow rate of water through the orifice.

The pressure test chamber was filled with distilled water and the PEEKsil tube was attached to the pressure chamber. The glass test tube covering the Peeksil tube was cleaned with alcohol and weighed using a digital scale to get a tare weight prior to the test. The pressure in the chamber was set to 15 psi with the use of a regulator. The supply line was opened and the start time for the test was recorded. The supply line was closed as soon as the first drop of water was dislodged from the Peeksil tube and the stop time was recorded. The glass tube was removed from the fixture and was weighed. This test was performed 3 times and the results were recorded. The pressure in the chamber was then changed to 5 psi and the test was repeated 3 more times and test result recorded. Peeksil was then replaced with EFD p/n: 7018395 tube, and a 1-minute test was performed at 5 psi, 10 psi & 25 psi and the results were recorded. EFD p/n: 7018395 was then replaced by EFD p/n: 5130-B tube and the test was performed at 5 psi, 10 psi & 25 psi and the results were recorded.

Last test was performed on a custom pin made by NT Medical with an orifice size of 0.003". Three tests were performed at 5 psi, 10 psi & 15 psi and the results were recorded. Table 1 summarizes the results.

TABLE 1

| Material | Trial # | ID (in) | Length (in.) | Pressure (psi) | Flow Rate (ml/hr) |
|---|---|---|---|---|---|
| Peeksil | 1 | 0.001" | 6 | 5 | 0.0072 |
| Peeksil | 2 | 0.001" | 6 | 5 | 0.0085 |
| Peeksil | 3 | 0.001" | 6 | 5 | 0.00817 |
| Peeksil | 4 | 0.001" | 6 | 15 | 0.0198 |
| Peeksil | 5 | 0.001" | 6 | 15 | 0.0191 |
| Peeksil | 6 | 0.001" | 6 | 15 | 0.0214 |
| Custom Pin | 7 | 0.003" | 1.1675 | 5 | 0.145 |
| Custom Pin | 8 | 0.003" | 1.1675 | 5 | 0.130 |
| Custom Pin | 9 | 0.003" | 1.1675 | 5 | 0.144 |
| Custom Pin | 10 | 0.003" | 1.1675 | 10 | 0.790 |
| Custom Pin | 11 | 0.003" | 1.1675 | 10 | 0.789 |
| Custom Pin | 12 | 0.003" | 1.1675 | 10 | 0.777 |
| Custom Pin | 13 | 0.003" | 1.1675 | 15 | 1.41 |
| Custom Pin | 14 | 0.003" | 1.1675 | 15 | 1.52 |
| Custom Pin | 15 | 0.003" | 1.1675 | 15 | 1.47 |
| Custom Pin | 16 | 0.003" | 1.1675 | 25 | 2.227 |
| Custom Pin | 17 | 0.003" | 1.1675 | 25 | 2.227 |
| Custom Pin | 18 | 0.003" | 1.1675 | 25 | 2.227 |
| EFD p/n: 5130-B | 19 | 0.006" | 0.73 | 5 | 90.65 |
| EFD p/n: 5130-B | 20 | 0.006" | 0.73 | 10 | 169.71 |
| EFD p/n: 5130-B | 21 | 0.006" | 0.73 | 25 | 354.84 |
| EFD p/n: 7018395 | 22 | 0.008" | 0.45 | 5 | 459.94 |
| EFD p/n: 7018395 | 23 | 0.008" | 0.45 | 10 | 719.38 |
| EFD p/n: 7018395 | 24 | 0.008" | 0.45 | 25 | 1274.96 |

Example 2

Manufacturing Procedure for the Break Three Silicone Capsule

Figure 5:
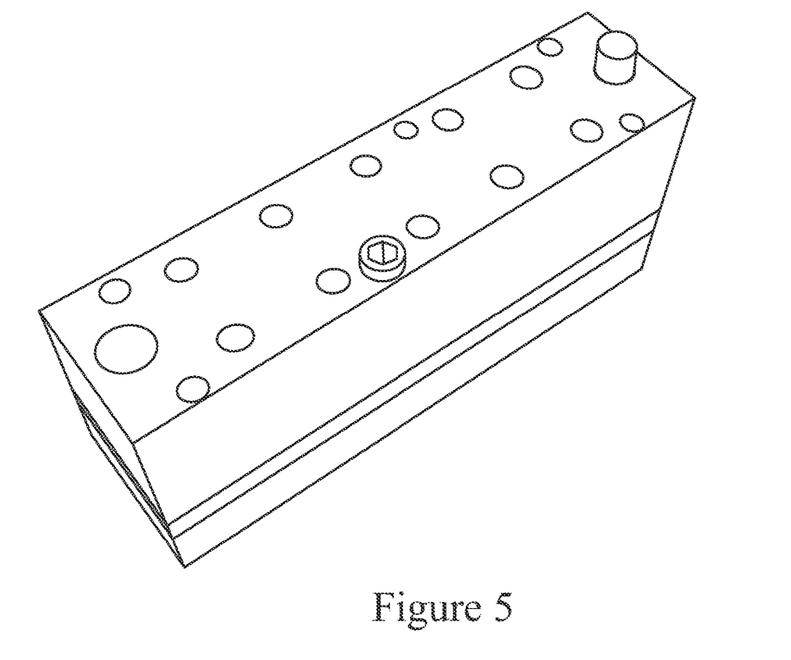
FIG. 5 illustrates a cavity casting mold used to manufacture a pill of the invention.
Figure 6:
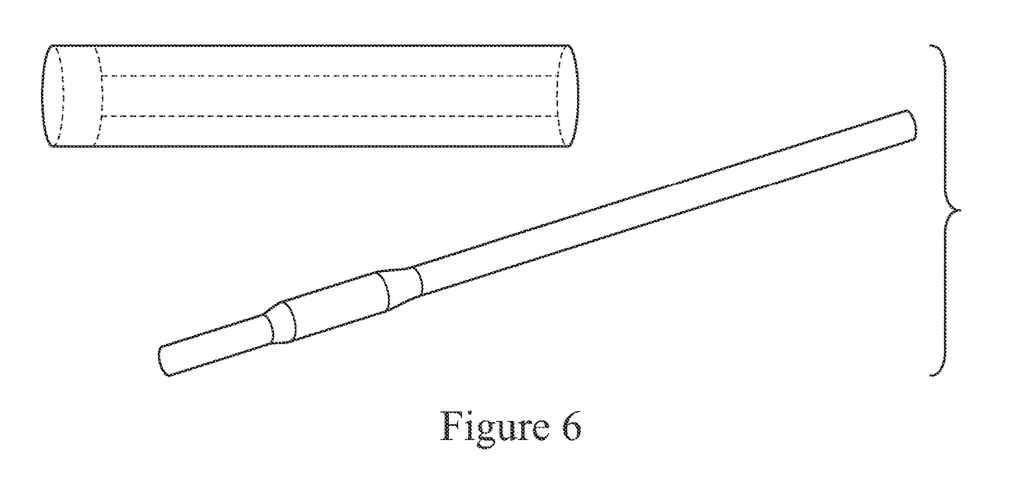
FIG. 6 illustrates a mandrel with a bulbous center used in the manufacture of a pill of the invention.

The materials included additional cure silicone rubber 40A (SORTA-CLEAR 40 supplied by Smooth-on); a 10 cavity casting mold (See FIG. 5); 0.074 mandreal with bulbous center (see FIG. 6); and a dispensing tip/syringe.

Figure 7:
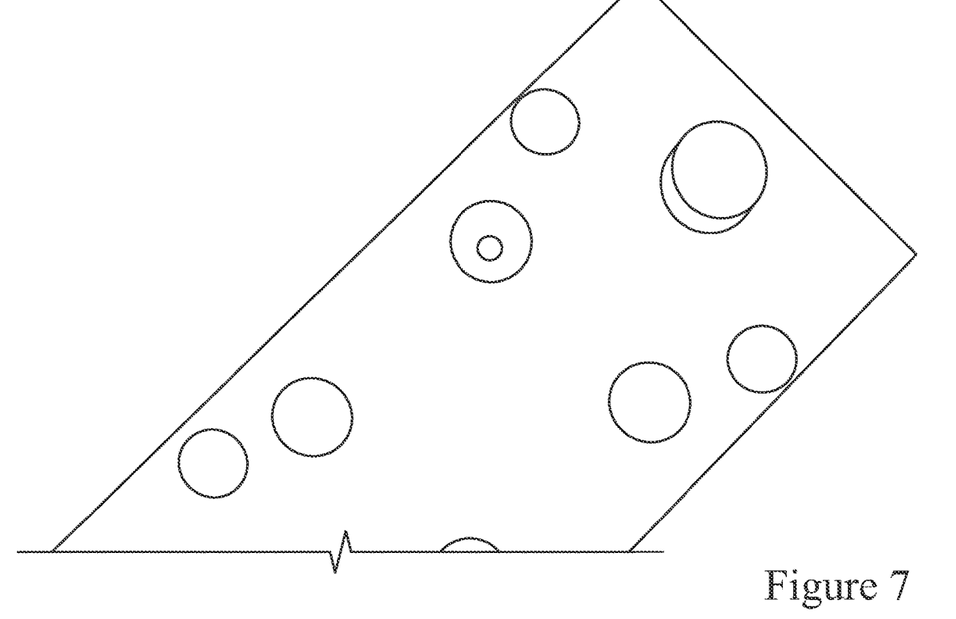
FIG. 7 illustrates the location of the pill in the cavity casting mold used in the manufacture of a pill of the invention.
Figure 8:
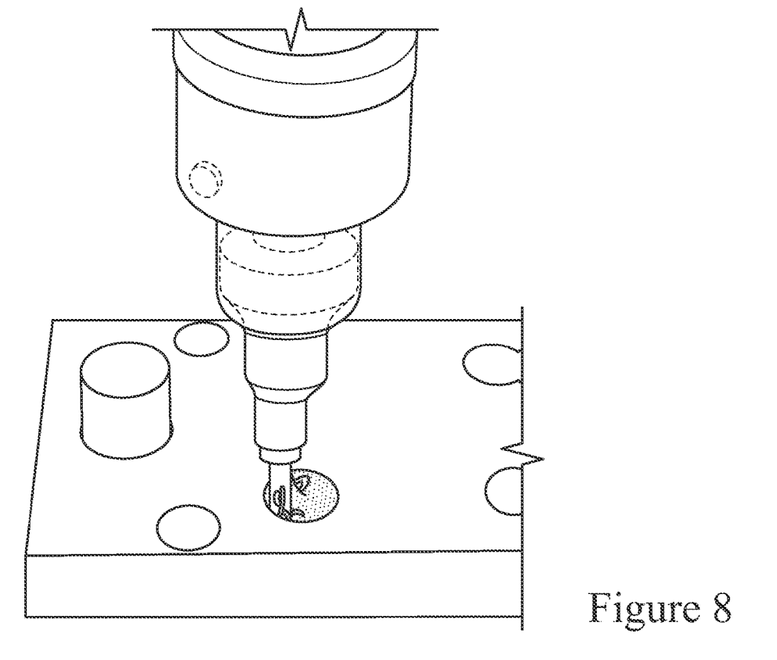
FIG. 8 illustrates the fill of a cavity with 15 gauge tip used in the manufacture of a pill of the invention.
Figure 9:
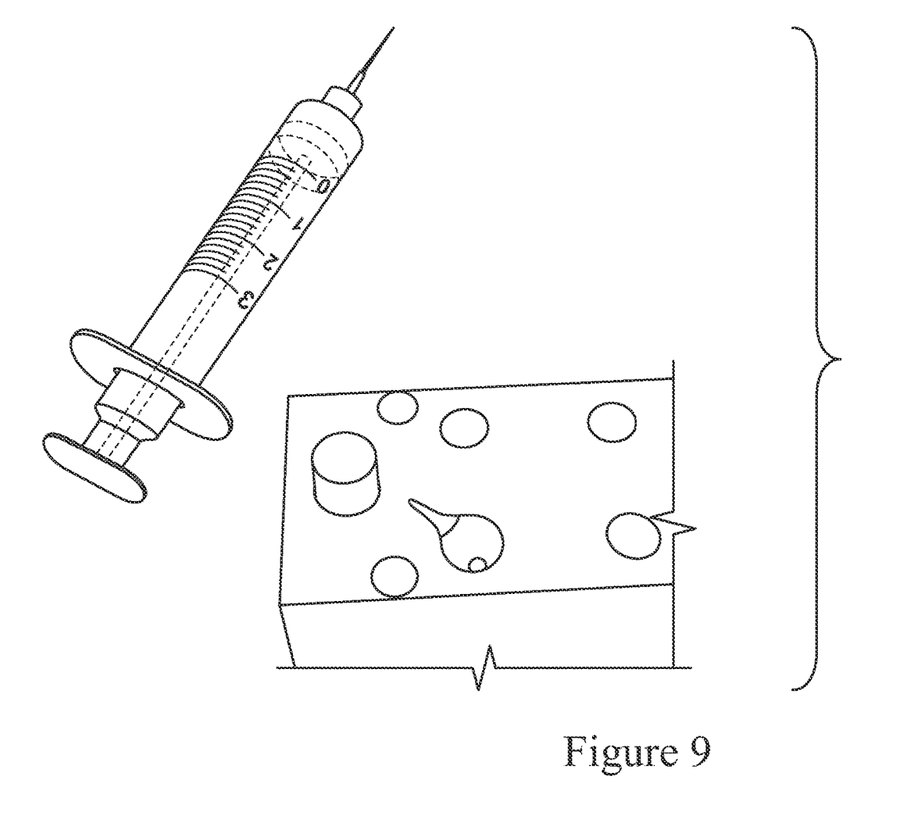
FIG. 9 illustrates a pill curing in a cavity casting mold used in the manufacture of a pill of the invention.

The procedure is a multistep procedure. First mix Part A and Part B per SORTA-CLEAR 40 mixing instructions, then fill syringe without introducing too many air bubbles. The pin should be 0.140 in below the surface as shown in FIG. 7, and the cavity is filled from floor of cavity with 15 gauge dispensing tip (see FIG. 8). Finally, let the material cure for 16 hours before removing from cavity (see FIG. 9).

Figure 10:
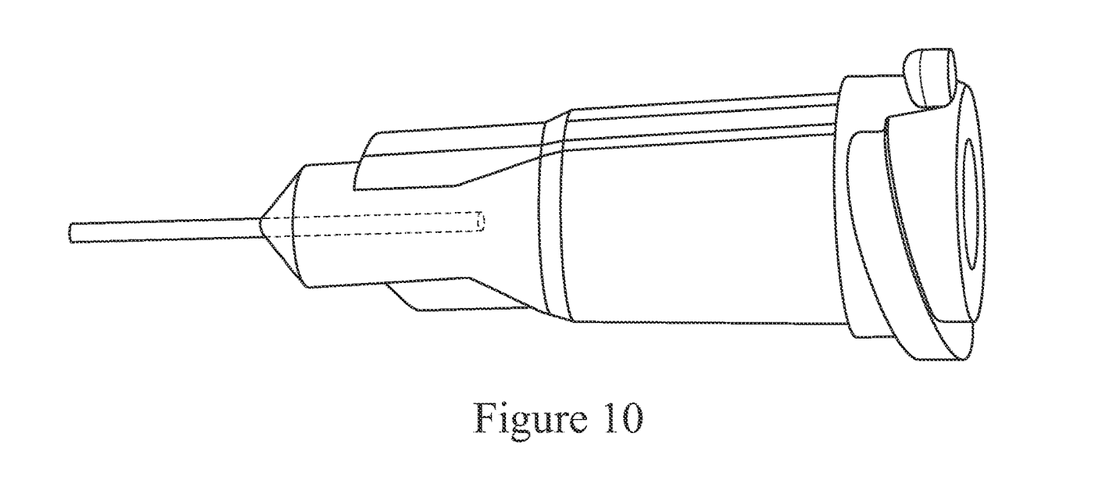
FIG. 10 illustrates a machined dispensing tip used in the manufacture of a pill of the invention.
Figure 11:
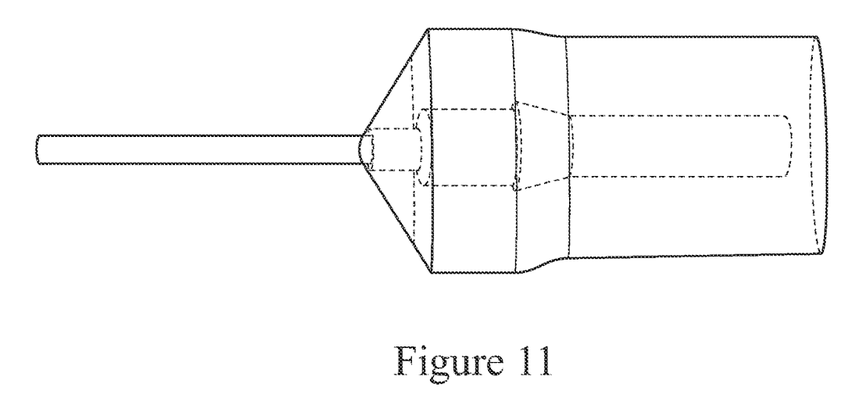
FIG. 11 illustrates a machined nozzle used in the manufacture of a pill of the invention.
Figure 12:
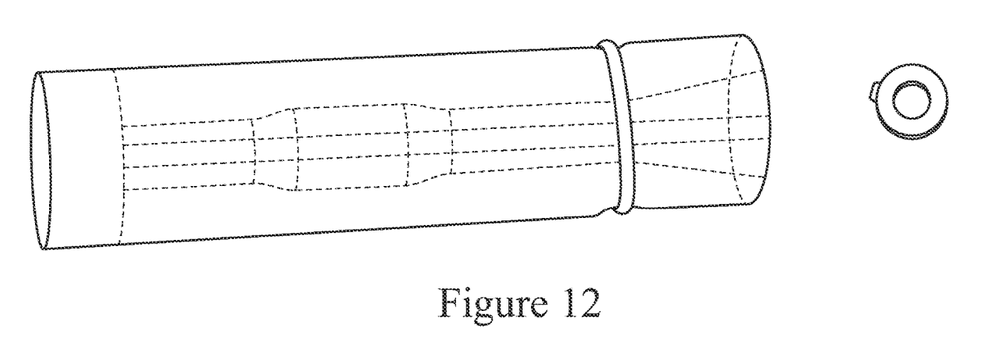
FIG. 12 illustrates an O-ring on a capsule used in the manufacture of a pill of the invention.
Figure 13:
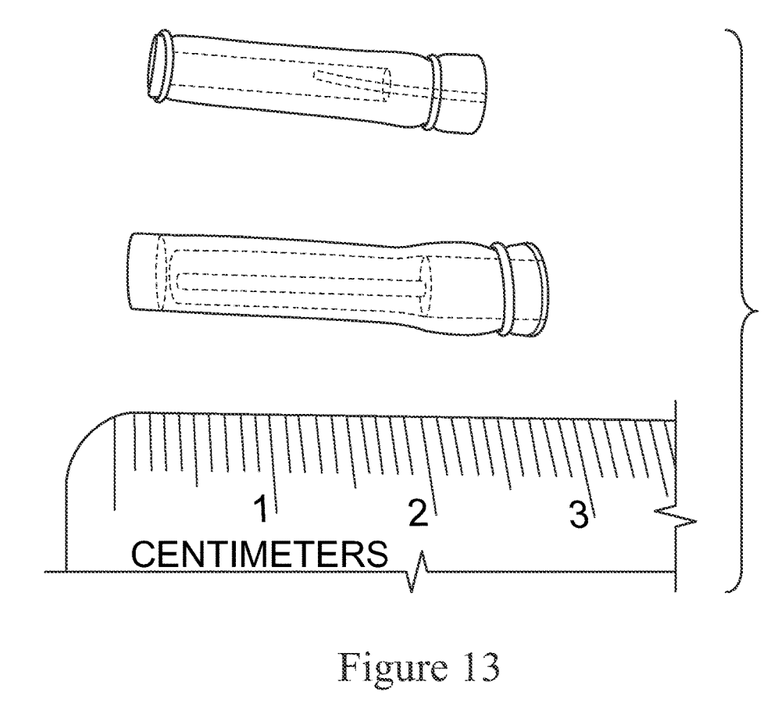
FIG. 13 illustrates a nozzle in a capsule used in the manufacture of a pill of the invention.
Figure 14:
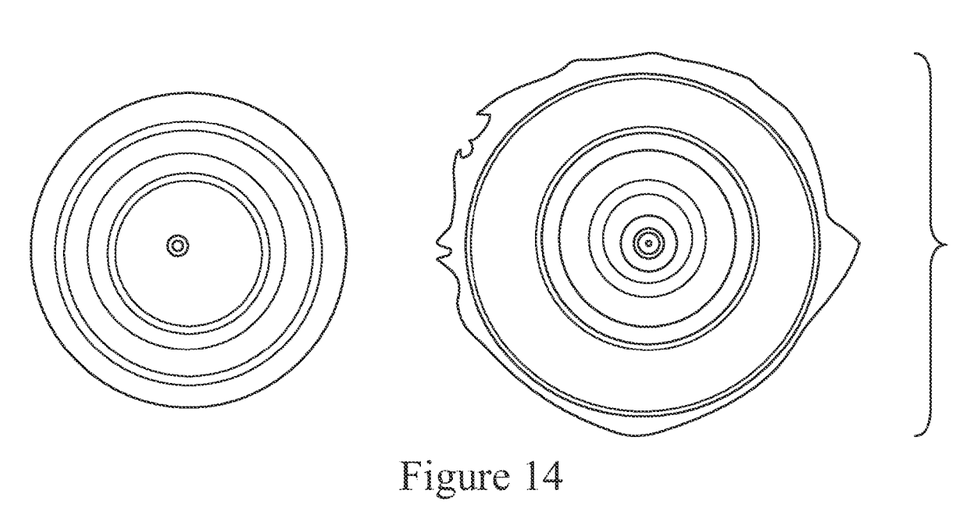
FIG. 14 illustrates the end view of a capsule used in the manufacture of a pill of the invention.
Figure 15:
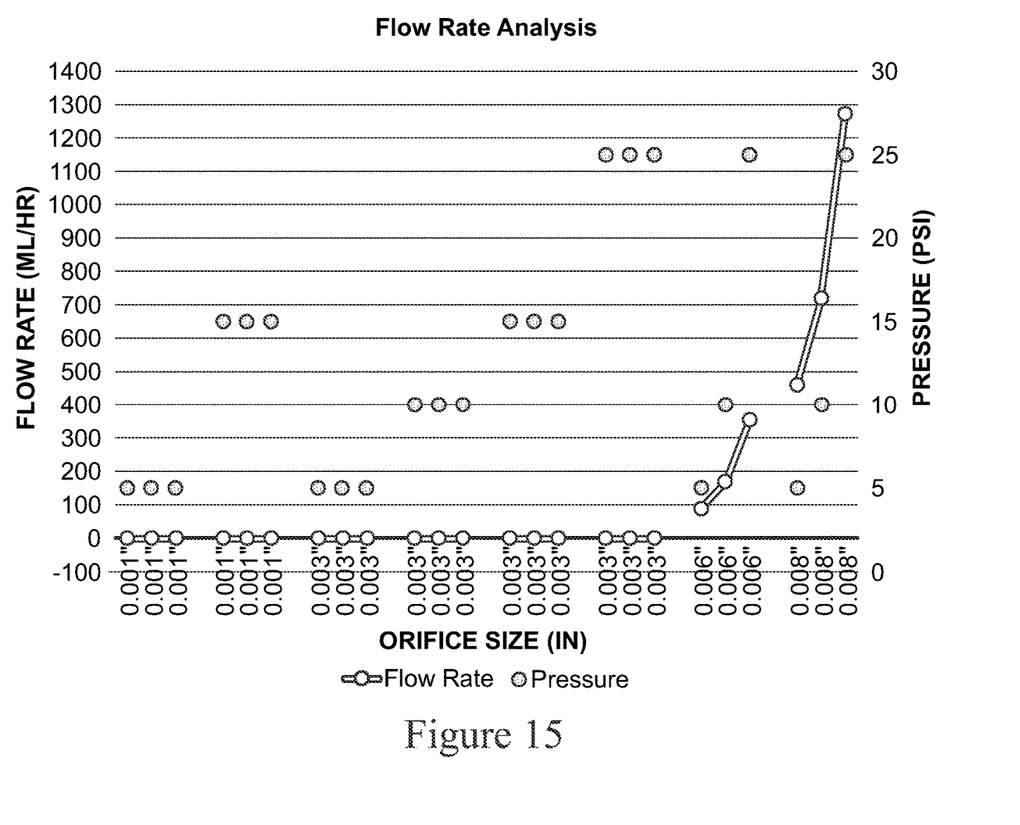
FIG. 15 illustrates in graph form the rate flow results of Table 1 in Example 1.

The assembly of the pill was straightforward. Machine (modify) down dispensing tip to a diameter of 0.125 inches (see FIGS. 10 and 11). Place rubber O-ring (0.050 ID) onto silicone capsule prior to insertion of nozzle (see FIG. 12). Place nozzle into silicone capsule with tubing inward till flush (see FIG. 13). The completed capsule had an end view as shown in FIG. 14.

It is appreciated that certain aspects and characteristics of the invention, which are, for clarity, described in the context of separate embodiments, may also be provided in combination in a single embodiment. Conversely, various aspects and characteristics of the invention, which are, for brevity, described in the context of a single embodiment, may also be provided separately or in any suitable sub-combination.

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A device for controlled-release delivery of an ingestible drug, comprising:
   a bio-compatible, non-digestible elastic housing comprising:
      a hollow interior configured to be filled with an ingestible drug,
      a filling port configured for pressurized filling of the hollow interior with the ingestible drug, and
      a delivery port for controlled delivery of the ingestible drug from the hollow interior,
   wherein the device, once the housing is filled with the ingestible drug, is configured to be swallowable by a user, and
   wherein the device, after delivery of the ingestible drug from the housing, is configured to exit the user's body through the digestive tract.

2. The device according to claim 1, wherein the housing is formed of a flexible elastomer.

3. The device according to claim 1, wherein the housing, once filled with the ingestible drug, has a pill or capsule shape.

4. The device according to claim 1, wherein the housing comprises an interior housing within an exterior housing, wherein:
   the interior housing comprises a hollow interior configured to be filled with the ingestible drug, and
   the exterior housing comprises a hollow interior configured to enclose the interior housing.

5. The device according to claim 4, wherein both the interior housing and the exterior housing are formed of a flexible elastomer.

6. The device according to claim 5, wherein the elastomer forming the exterior housing is less flexible than the elastomer forming the interior housing.

7. The device according to claim 1, wherein the filling port has a one-way filling valve that prevents the ingestible drug from exiting the hollow interior therethrough.

8. The device according to claim 1, wherein the delivery port has a seal or closure that may be closed while the hollow interior is being filled with the ingestible drug and may be removed or opened prior to swallowing of the device by a user.

* * * * *